United States Patent
Brackett et al.

(10) Patent No.: US 6,210,327 B1
(45) Date of Patent: Apr. 3, 2001

(54) METHOD AND APPARATUS FOR SENDING ULTRASOUND IMAGE DATA TO REMOTELY LOCATED DEVICE

(75) Inventors: Charles C. Brackett, Waukesha; Gregory C. Stratton, Wauwatosa; James S. Lehouillier, Waukesha; Jeannette M. Eichholz, West Allis; Takao Shiibashi, Brookfield, all of WI (US)

(73) Assignee: General Electric Company, Milwaukee, WI (US)

( * ) Notice: Subject to any disclaimer, the term of this patent is extended or adjusted under 35 U.S.C. 154(b) by 0 days.

(21) Appl. No.: 09/300,876

(22) Filed: Apr. 28, 1999

(51) Int. Cl.[7] ....................................................... A61B 8/00
(52) U.S. Cl. ........................................... 600/437; 600/407
(58) Field of Search ..................................... 600/437, 407, 600/410, 443, 447; 128/903, 922; 395/701, 703, 705, 280, 680, 726; 345/156, 329, 520; 705/2, 3; 707/200, 500, 513; 713/100

(56) References Cited

U.S. PATENT DOCUMENTS

| | | | |
|---|---|---|---|
| 4,688,168 | * | 8/1987 | Gudaitis et al. ...................... 710/107 |
| 4,853,875 | * | 8/1989 | Brown .................................. 709/228 |
| 5,124,789 | * | 6/1992 | Hiyama et al. ......................... 358/98 |
| 5,235,510 | * | 8/1993 | Yamada et al. ....................... 600/300 |
| 5,321,520 | * | 6/1994 | Inga et al. ............................. 358/403 |
| 5,469,353 | * | 11/1995 | Pinsky et al. ......................... 364/401 |
| 5,654,555 | * | 8/1997 | Buytaert et al. ...................... 250/581 |
| 5,655,084 | * | 8/1997 | Pinsky et al. ......................... 395/203 |
| 5,668,998 | * | 9/1997 | Mason et al. ......................... 395/701 |
| 5,689,443 | * | 11/1997 | Ramanathan ......................... 702/183 |
| 5,806,005 | * | 9/1998 | Hull et al. ............................... 348/17 |
| 5,851,186 | * | 12/1998 | Wood et al. .......................... 600/437 |
| 5,897,498 | | 4/1999 | Canfield et al. ...................... 600/437 |
| 5,959,678 | * | 9/1999 | Callahan et al. ....................... 345/27 |
| 5,971,923 | * | 10/1999 | Finger ................................... 600/437 |
| 5,986,662 | * | 11/1999 | Argiro ................................... 345/424 |
| 6,117,079 | * | 9/2000 | Brackett et al. ...................... 600/437 |

* cited by examiner

*Primary Examiner*—Francis J. Jaworski
(74) *Attorney, Agent, or Firm*—Dennis M. Flaherty; Christian G. Cabou; Phyllis Y. Price (57) ABSTRACT

A computerized ultrasound imager is programmed with software that enables a "Live Imaging" mode. "Live Imaging" refers to the ability to keep a network association (between the imager and a remote device) open throughout the course of an examination of a patient. Each time the operator presses a Print/Store button configured to a storage device, the frozen image will be automatically sent to the remote device via the open connection. The "Live Imaging" association is closed when the system operator presses an "End Exam" button on the keyboard. In the case where the remote device is a printer configured to receive multi-image film sessions, pressing the "End Exam" button also forces the transfer of any partially filled film session from the imager to the printer.

15 Claims, 6 Drawing Sheets

DEVICE CONFIGURATION    PAGE    1 of 11

NAME [PRINTER A]
IP ADDR [0] . [0] . [0] . [0]    COLOR [COLOR]    AE TITLE [           ]
PORT [104]    RETRY INTERVAL [10] SEC    DEVICE TYPE [PRINTER]
RETRIES [1]    ACTIVATE [YES]—66    TIMEOUT [10] SEC
ECHO [ECHO ON]

PRINTER SETUP
FORMAT        [1 X 1]            ORIENTATION    [PORTRAIT]
SIZE          [8in x 10in]       MEDIA TYPE     [PAPER]
COPIES        [1]                BORDER         [BLACK]
PRIORITY      [HIGH]             EMPTY          [BLACK]
MIN DENSITY   [0]                MAX DENSITY    [0]
TRIM          [NO]               DESTINATION    [MAGAZINE]
MAGNIFICATION [REPLICATE]
SMOOTH        [NONE]
FILM SESSION LABEL [          ]
CONFIGURATION STRING [          ]

WORKLIST SETUP                   STORAGE SETUP
POLLING RATE [0] MINUTES         TYPE [AUTOMATIC]
                                 LIVE IMAGING [OFF]—67
                                 ROI  SIZE TO PAGE
TKBL/RET TO POSITION    SET TO SELECT    EXIT  TO SAVE

FIG.5

|  | DEVICE CONTROL | | | | PAGE 5 OF 6 |
|---|---|---|---|---|---|
|  | P1 | P2 | SP1 | SP2 TYPE | STATUS |
| LOCAL STORAGE | | | | | |
| COLOR | * | | | | |
| GRAY | | * * | | | FRAMES: 100/297 |
| HARD DISK | | | * | *  ←76 | FRAMES: 238/705 |
| MOD | | | | | |
| | | | | | |
| DICOM DEVICES | | | | | |
| PRINTER A | * | | | * | |
| PRINTER B | | | * | | |
| STORAGE A | * | | | * | |

TKBL/RET TO POSITION    SET TO SELECT    ROI SIZE TO PAGE
EXIT TO SAVE

FIG.6

METHOD AND APPARATUS FOR SENDING ULTRASOUND IMAGE DATA TO REMOTELY LOCATED DEVICE

FIELD OF THE INVENTION

This invention generally relates to imaging systems used in medical diagnostics. In particular, the invention relates to the transfer of digital images from an ultrasound imaging system over a network to remote devices for archiving and/or printing.

BACKGROUND OF THE INVENTION

Conventional ultrasound imagers create two-dimensional images of biological tissue by scanning a focused ultrasound beam in a scan plane and for each transmitted beam, detecting the ultrasound wave energy returned along a respective scan line in the scan plane. A single scan line (or small localized group of scan lines) is acquired by transmitting focused ultrasound energy at a point, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. A scan line's resolution is a result of the directivity of the associated transmit and receive beam pair.

A B-mode ultrasound image is composed of multiple image scan lines. The brightness of a pixel on the display screen is based on the intensity of the echo returned from the biological tissue being scanned. The outputs of the receive beamformer channels are coherently summed to form a respective pixel intensity value for each sample volume in the object region or volume of interest. These pixel intensity values are log-compressed, scan-converted and then displayed as a B-mode image of the anatomy being scanned.

If the ultrasound probe is swept over an area of body, a succession of image frames (corresponding to spaced slices intersecting the body being examined) can be displayed on the monitor. In one type of ultrasound imaging system, a long sequence of the most recent images are stored and continuously updated automatically in a cine memory on a first-in, first-out basis. The cine memory is like a circular image buffer that runs in the background, capturing image data that is displayed in real time to the user. The cine memory acts as a buffer for transfer of images to digital archival devices via the host computer. When the user freezes the system (by operation of an appropriate device on an operator interface), the user has the capability to view image data previously captured in cine memory. The image loop stored in cine memory can be reviewed on the display monitor via trackball control incorporated in the operator interface, and a section of the image loop can be selected for hard disk storage.

If the transducer probe was moving during image acquisition, the succession of image frames stored in cine memory form a three-dimensional data volume of image information. This data volume can be used by the system computer to project a three-dimensional view of the area of interest. This projected image can be returned to memory and then displayed on the monitor. Any acquired or projected image can be stored internally on the system hard disk or on a magneto-optical disk (MOD) inserted in a disk drive.

In addition to storing images internally, modern ultrasound imaging systems need to be able to transfer images to various types of remote devices via a communications network. To successfully transfer images, the relevant networking features of the ultrasound imager must be compatible with the networking features of the destination remote device. In particular, the ultrasound imager must place the data to be transferred in a format which can be handled by the destination remote device. An attempt to accomplish the foregoing is the adoption of the DICOM (Digital Imaging and Communications in Medicine) standards, which specify the conformance requirements for the relevant networking features. The DICOM standards are intended for use in communicating medical digital images among printers, workstations, acquisition modules (such as an ultrasound imaging system) and file servers. The acquisition module is programmed to transfer data in a format which complies with the DICOM standards, while the receiving device is programmed to receive data which has been formatted in compliance with those same DICOM standards.

DICOM involves more than digital image transfer. DICOM functionality includes the following Service Classes: archive/transfer images: store (across network); archive/interchange images: media storage; query for information and retrieve images; make image hard copies: print management; patient, study and results management; radiology information system modality: worklist management; and test connectivity: verification. A fundamental concept employed in DICOM is "Services on Objects". One example of an "Object" is an ultrasound image. Two examples of a "Service" are the "Store" and "Query/Retrieve" functions. In DICOM, methods of operating on information objects are referred to as "Service Object Pair Classes" (SOP Classes). Examples of SOP Classes are "Store an ultrasound image", "Print an ultrasound image", "Find which studies there are for a certain patient", "Retrieve all studies of a certain patient" and "Retrieve a worklist". Unique Identifiers (UIDs) are defined for all SOP Classes. UIDs are also given to all studies, series and images. These UIDs are, for instance, used for retrieval. In the DICOM vernacular, a patient has a study which comprises a study component, e.g., examination using a particular modality. Images acquired in sequence in the course of a study on a patient form a series of objects.

The DICOM system is based on the client/server concept. The device which uses a service (on objects) is the client device, while the device which provides the service is the server device. The client device is referred to as a Service Class User (SCU), while the server device is referred to as a Service Class Provider (SCP). The SCU sends a Service Request to the SCP over a local area network (LAN). The SCP sends back a response to the SCU over the same LAN. If the response is affirmative and a communications syntax is agreed upon, an association between the SCU and the SCP is opened and data can be transferred between the two devices. In the DICOM system a device is not limited to one role: it can be both SCU and SCP at different times.

The DICOM system is designed to facilitate the communication of digital images of different types, e.g., X-ray, computerized tomography, magnetic resonance and ultrasound imaging. In an ultrasound imager having conventional DICOM capability, three local real-world activities occur: Image Send, Image Print and Remote Verification. Image Send and Image Print can be done in either automatic or manual mode. Verification of remote DICOM devices configured on the ultrasound imager is performed when the imager is powered up or when requested by the system operator.

All DICOM activities are handled in a queued manner by application software running on a host computer incorporated in the imager. In one type of ultrasound imager, the user can select any image in cine memory to be sent in DICOM format via a LAN to a remote device having DICOM capability. The host computer of the ultrasound imaging system is programmed with DICOM system software which facilitates transmission of image frames from the cine memory to the remote DICOM device via the host computer hard disk and the LAN.

In the conventional ultrasound imager, Image Send can be used in automatic or manual mode, depending on the user configuration. When automatic mode is configured, console keys are used to capture the image and to store it on the hard disk. The request is queued to a DICOM queue manager (preferably implemented in software), which requests an association with the destination remote device. After the association with the remote device has been opened, the queue manager "pushes" the image to the remote device without user intervention. The transfer is done in the background while scanning or other operator activities continue. In manual mode, the captured images are archived on the hard disk or on a MOD during the exam(s). Upon completion of the exam(s) the images are tagged using an archive menu and queued to any of the network devices that have been configured on the imager. The images are sent sequentially in the background while scanning or other operator activities proceed. Image Print works much the same way as Image Send, in both automatic and manual modes, the only difference being that the destination device is a printer.

In order to accomplish image transfer, the ultrasound imaging system must know the configuration of the destination remote device prior to attempting to communicate with that device. The configuration data for the destination remote device is typically inputted to the ultrasound imager during software installation by a field engineer, although the DICOM network can be configured at any time. When the imager receives an instruction to transmit data to a particular remote device from the system operator, the imager software converts the image data to be transferred into the DICOM format required by the destination remote device, based on the configuration data for that device stored in system memory. The imager also sends a request over the network to the destination remote device to open an association, i.e., to connect the imager to the destination remote device. If the remote device responds in the affirmative, the imager and remote device then agree on which SOP Class is to be used and which device will act as the server and which as the client. The ultrasound imager also selects the appropriate encoding syntax from those accepted by the remote device. Other communication parameters are also negotiated.

After the DICOM communications protocol has been settled, the association is opened and the imager attempts to send the DICOM-formatted image file (object) to the remote device via the network. The transfer is done in the background while scanning or other operator activities continue. If the remote device is a storage device, each image file is transferred singly in response to a Send request inputted by the operator. The conventional imager with DICOM capability will open an association with a storage device in response to each "send to a storage device" instruction. If a transfer is successful, the association for that transfer is immediately closed. If the remote device is a printer configured to print multi-image film, then a number of images are accumulated to make up a multi-image film and an association is opened in response to a Send instruction when a number of images sufficient to fill the multi-image film have been accumulated. After the full film session of images has been transmitted, the association between the imager and printer is closed.

If the destination remote device sends back a message indicating successful receipt of the transmitted data, the DICOM-formatted image file can be deleted from the imager memory. Alternatively, the system operator can instruct the imager to retain the DICOM-formatted image file on the imager hard disk or to store it on a MOD inserted in the imager.

The remote device to which the ultrasound imager sends data can be a printer, a storage device or other device. If the operator interface of the imager has only one configurable Print/Store button, then that button will be configured to initiate data transfer to the destination remote device. The configuration data for the remote device will indicate the type of device to the imager and then the imager will format the data being transferred accordingly. If the operator interface has multiple Print/Store buttons, then each button can be configured to initiate data transfer to a respective remote device. Data transfer to any one of those configured remote devices can then be initiated by pressing the appropriate Print/Store button.

In addition to the digitized image (i.e., pixel data), the DICOM object transferred from the ultrasound imager also includes attribute information. For example, the attribute information may include patient attributes (e.g., patient name and patient identification number), study attributes (e.g., accession number and study date), series attributes (e.g., modality type and series date), and image attributes (e.g., image type and numbers of rows and columns). Each attribute has a name, a value representation and a tag. A tag is a number unique to the attribute. The value representation defines what type of value the attribute can have (e.g., a 64-character string, binary data, etc.).

In accordance with DICOM standards, there are three types of attributes. Type 1 comprises attributes which are mandatory and must always be present with a value; Type 2 comprises attributes which are mandatory but are allowed to be empty; and Type 3 comprises attributes which are optional and are also allowed to be empty. An incompatibility between two devices may arise, for example, if the receiving device requires that a Type 3 attribute be transmitted while the sending device does not include that attribute in its transmission. As a result, even if both devices are configured in accordance with current DICOM standards, the data transfer cannot occur. Thus, even mutual conformance to DICOM standards does not guarantee that two devices can be compatibly connected to each other.

In accordance with a further aspect of the DICOM system as currently implemented, an ultrasound imaging system can retrieve a worklist from a Radiology Information System (RIS) at a hospital via the LAN. The retrieved worklist may, e.g., comprise all patients to be examined on a particular day using that particular ultrasound imager. The worklist includes the following information for each patient: name, identification number, sex, birth date, accession number, study data, etc. The information retrieval is initiated by the ultrasound imager. In response to this query, the RIS transmits the worklist to the ultrasound imager, which stores it in memory. This worklist is then available for viewing by the sonographer. The patient currently being examined can be selected from the worklist.

In order to protect against image data loss due to a failed attempt to send that image data from the imager to a remote device on the network, the user must also store that image data in the local storage device, e.g., the computer hard drive. These images stored in the hard drive must be manually removed at the end of the day or when the hard drive is full. This procedure has the disadvantages that the wrong images could be accidentally deleted; sorting through the images is difficult and prone to user error, which could result in the wrong images being printed; and more time between patient exams is required in order to perform manual image cleanup. In addition, if the imager's primary storage system or printer has a failure that cannot be corrected immediately and if the imager is implemented in such a way that the image data for the failed data transfer is lost, then the result is that the patient being examined must be rescheduled and re-scanned.

Because the DICOM capability is implemented in software, these features of the ultrasound imaging system can be readily upgraded. One goal of such upgrades is to increase the efficiency of the system operator by making the system simpler to operate, e.g., by requiring fewer manipulations to activate a particular operation. Another goal of system upgrades is to increase the ability of the imager to connect rapidly, efficiently and reliably to remote devices on the network, i.e., to increase connectivity.

SUMMARY OF THE INVENTION

The invention disclosed herein relates generally to imaging systems which acquire multiple frames of images in succession in the course of a patient examination. In particular, the invention relates to ultrasound imaging systems capable of transferring images to remotely located devices via a DICOM network. Although the preferred embodiment of the invention communicates with remote devices using the DICOM standard, the invention has application with any digital image communications standard or protocol.

In accordance with one aspect of the invention, a computerized ultrasound imager is programmed with software that provides a "Live Imaging" mode, which can be activated by clicking on a virtual representation of a "Live Imaging" toggle switch displayed on a menu. "Live Imaging" refers to the ability to keep a network association (between the imager and a remote device) open throughout the course of an examination of a patient, i.e., as images are acquired. This feature allows more efficient image transfer because the association need not be opened and closed for every image sent to a remote device, thereby reducing transfer time on the network. Each time the operator presses a Print/Store button configured to a storage device, the frozen image will be automatically sent to the remote device via the open connection. Each time the operator presses a Print/Store button configured to a printing device which prints multi-image film sessions, the frozen images are accumulated until the film session is full. The full film session is transferred to the printing device automatically upon acquisition of the last image needed to fill the film session, without the need for input by the operator of a further command. After the full film session of images has been transmitted, the association between the imager and printer is held open.

In accordance with a further aspect of the invention, the "Live Imaging" association is kept open until the system operator presses an "End Exam" button on the keyboard. Depression of the "End Exam" button closes all open associations between the imager and remote devices. In the case where the remote device is a printer configured to receive multi-image film sessions, pressing the "End Exam" button also forces the transfer of any partially filled film session from the imager to the printer for printing. The response to depression of the "End Exam" button on the keyboard is preferably implemented in software.

DETAILED DESCRIPTION OF THE PREFERRED EMBODIMENTS

Figure 1:
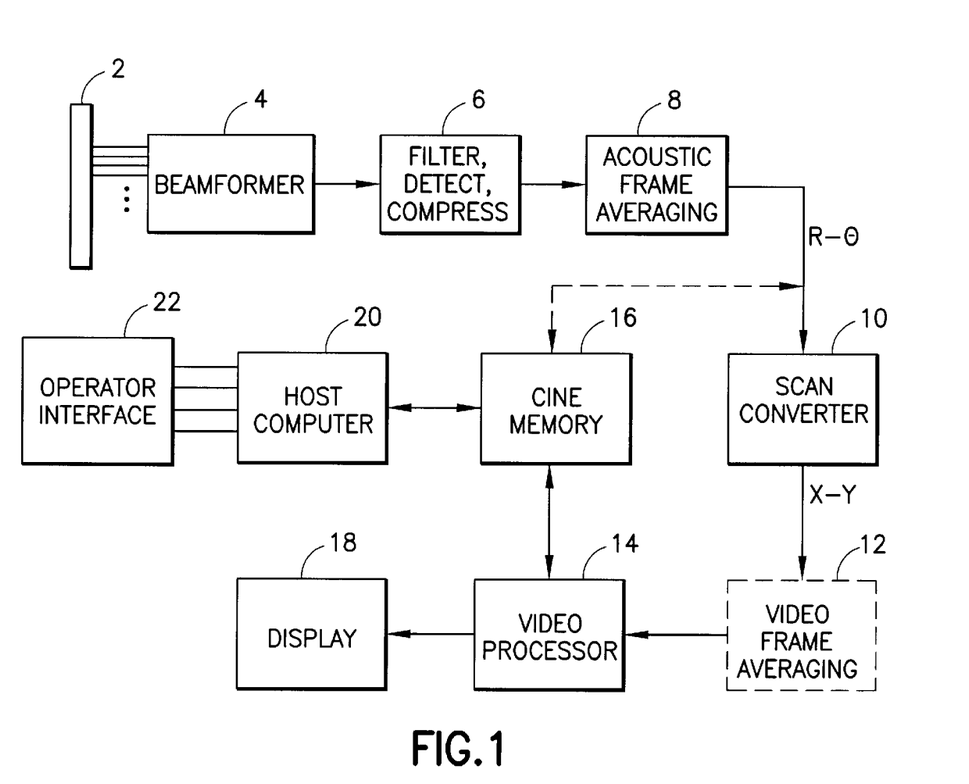
FIG. 1 is a block diagram showing a conventional ultrasound imaging system of the type which can be programmed to have DICOM capability.

FIG. 1 shows a conventional computerized ultrasound imaging system which can be programmed to communicate with remote devices over a network in conformance with the DICOM standard. The type of imaging system depicted in FIG. 1 create two-dimensional B-mode images of tissue in which the brightness of a pixel is based on the intensity of the echo return. The basic signal processing chain is as follows.

An ultrasound transducer array 2 is activated to by a transmitter in a beamformer 4 to transmit an acoustic burst which is focused at a point along a scan line. The return RF signals are detected by the transducer elements and then dynamically focused to form a receive beam by a receiver in the beamformer 4. The receive beamformer output data (I/Q or RF) for each scan line is passed through a B-mode processing chain 6, which preferably includes demodulation, filtering, envelope detection, logarithmic compression and edge enhancement.

Depending on the scan geometry, up to a few hundred receive vectors may be used to form a single acoustic image frame. To smooth the temporal transition from one acoustic frame to the next, some acoustic frame averaging 8 may be performed before scan conversion. In general, the log-compressed display data is converted by the scan converter 10 into X-Y format for video display. On some systems, frame averaging may be performed on the X-Y data (indicated by dashed block 12) rather than the acoustic frames before scan conversion, and sometimes duplicate video frames may be inserted between acoustic frames in order to achieve a given video display frame rate. The scan-converted frames are passed to a video processor 14, which maps the video data using a gray-scale mapping. The gray-scaled image frames are then sent to a video monitor 18 for display.

System control is centered in a host computer 20, which accepts operator inputs through an operator interface 22 and in turn controls the various subsystems. (In FIG. 1, only the image data transfer paths are depicted.) The operator interface comprises a keyboard, a trackball, a multiplicity of pushbuttons, and other input devices such as sliding and rotary knobs.

During imaging, a long sequence of the most recent images are stored and continuously updated automatically in a cine memory 16. Some systems are designed to save the R-θ acoustic images (this data path is indicated by the dashed line in FIG. 1), while other systems store the X-Y video images. The image loop stored in cine memory 16 can be reviewed via trackball control, and a section of the image loop can be selected for hard disk storage.

For an ultrasound imaging system which has been configured with a free-hand three-dimensional imaging capability, the selected image sequence stored in cine memory 16 is transferred to the host computer 20 for three-dimensional reconstruction. The result is written back into another portion of the cine memory, from where it is sent to the display system 18 via video processor 14.

Figure 2:
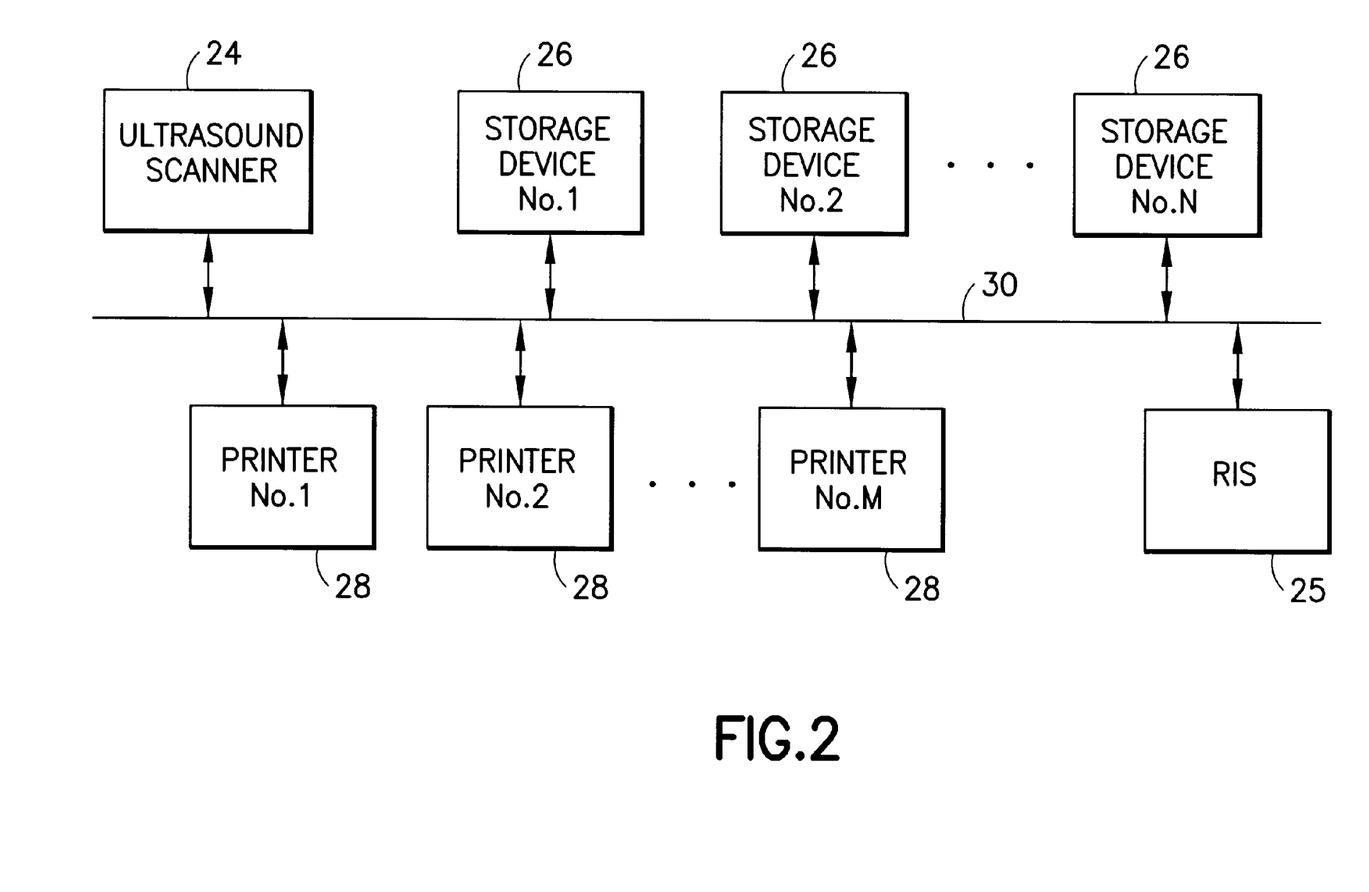
FIG. 2 is a block diagram showing a typical DICOM network.

FIG. 2 generally depicts a simplified DICOM network having an ultrasound scanner 24, a RIS 25, N storage devices 26, and M printing devices 28, all connected to a LAN 30. It will be readily appreciated that this diagram represents a simplified example of a DICOM network and that an actual DICOM network in the real world will have many more devices connected to the LAN, including modalities other than ultrasound imaging systems. The present invention is incorporated in an ultrasound imager (scanner) having the built-in capability to communicate with any one or more of the devices 25, 26 and 28 in conformance with the DICOM requirements.

Figure 3:
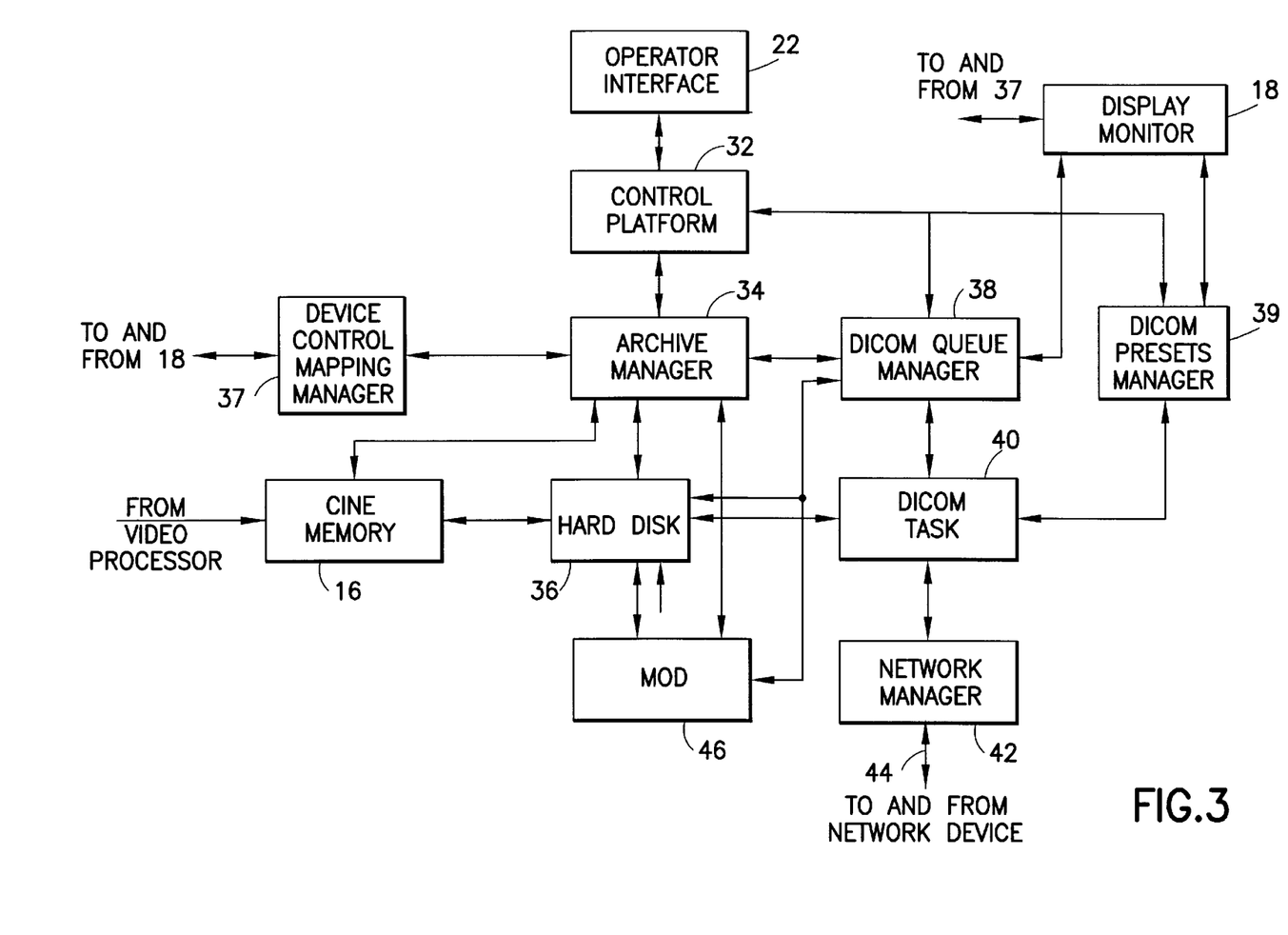
FIG. 3 is a block diagram generally depicting the hardware and software of an ultrasound imaging system in accordance with the preferred embodiment of the present invention.

A portion of such an ultrasound imager is generally depicted in FIG. 3. At the outset it should be appreciated that all of the blocks depicted in FIG. 3, with the exceptions of the cine memory 16, the display monitor 18 and the operator interface 22, are preferably incorporated in the host computer (depicted in FIG. 1 as block 20). It should be further appreciated that blocks 32, 34, 37–40 and 42 in FIG. 3 are preferably implemented as software.

In the system depicted in FIG. 3, commands inputted via the operator interface 22 are detected and processed by a control platform 32. In return, the control platform will provide signals to the operator interface which activate various visual indicators on the operator interface to indicate the status of various functions. In response to manipulation of the appropriate key or appropriate set of keys by the operator, the DICOM presets manager 39 will display a "Device Configuration" menu (shown in FIG. 5) on the display monitor 18. The operator then enters configuration data for the first destination remote device (e.g., "Printer A" in FIG. 5) via the operator interface. Depending on whether the device being configured is a printer or storage device, the Device Type field on the Device Configuration menu will be filled in with either a "Printer" or a "Storage" entry. If the device being configured is a printer which prints multi-image film sessions, then the Format field in the "Printer Setup" section on the Device Configuration menu will be filled in with numbers indicating the printing format of the multi-image printer (e.g., "3×5" in the case of Printer A). For single-image printers, the entry in Format field 65 will be "1×1". A separate page of the "Device Configuration" menu will be "filled in" for each remote device which the operator wishes to configure.

The imager shown in FIG. 3 is designed to communicate with a configured remote device only if that device has been "activated". Activation causes the DICOM presets manager 39 to configure one of a multiplicity of DICOM tasks 40 in accordance with configuration data entered into the system for the associated remote device. That particular DICOM task will thereafter remain configured for that type of remote device until reconfigured for a different device. Other DICOM tasks are configured for other remote devices.

Figure 5:
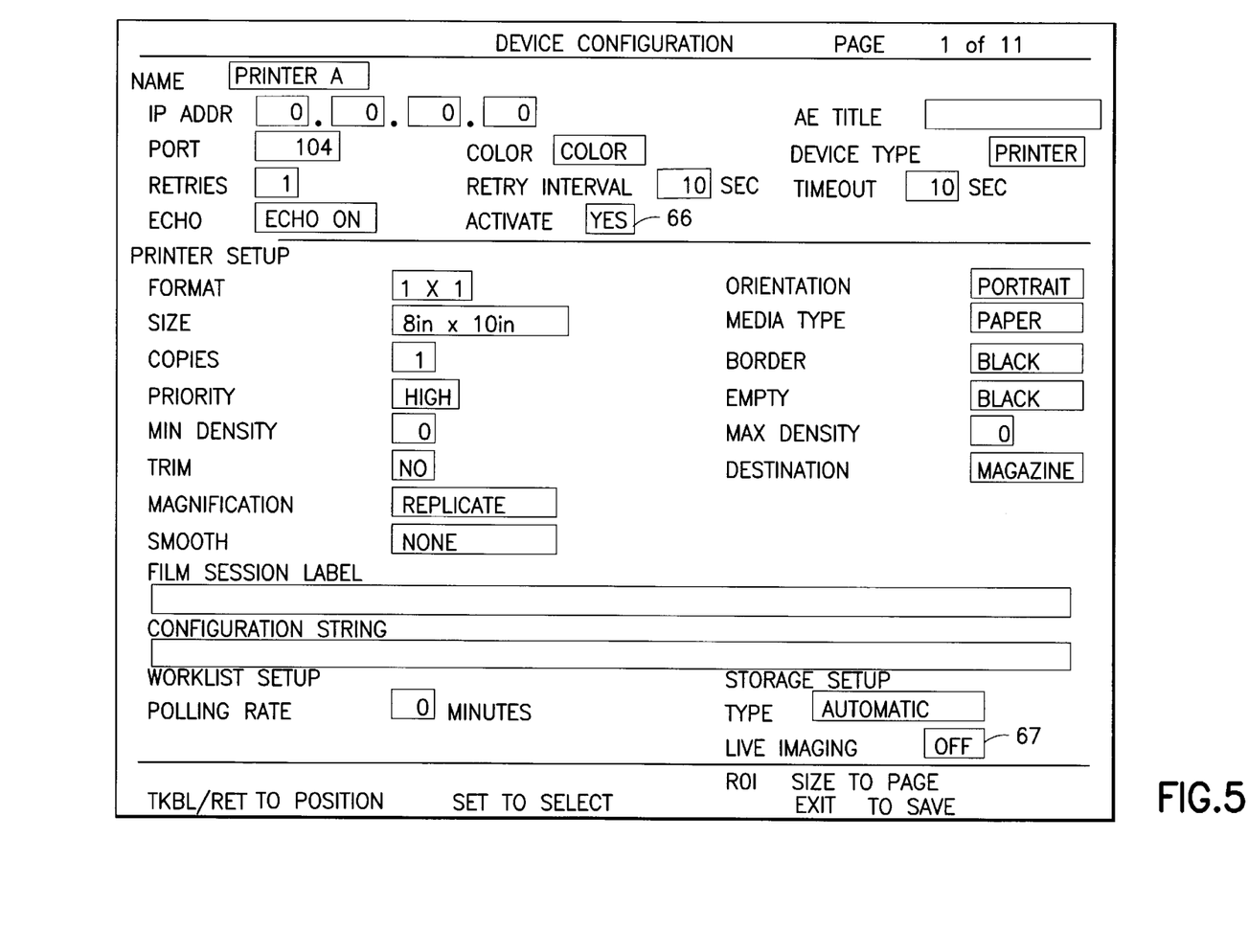
FIG. 5 is a schematic reproducing a "Device Configuration" menu which can be called up on the display monitor during configuration of the imaging system in accordance with the preferred embodiment of the invention.

One way of activating a remote device is to click on the Activate field 66 on the Device Configuration menu to toggle the "Activate" state on. A second click on field 66 will toggle the "Activate" state off, and so forth.

In addition, for each remote device being configured, the operator may click on the box 67 to switch the "Live Imaging" mode on. A second click on box 66 will toggle the "Live Imaging" mode off, and so forth. The following description of the structure and operation of the preferred embodiment assumes that the "Live Imaging" mode is activated and that the remote receiving device accepts images one image at a time.

Figure 6:
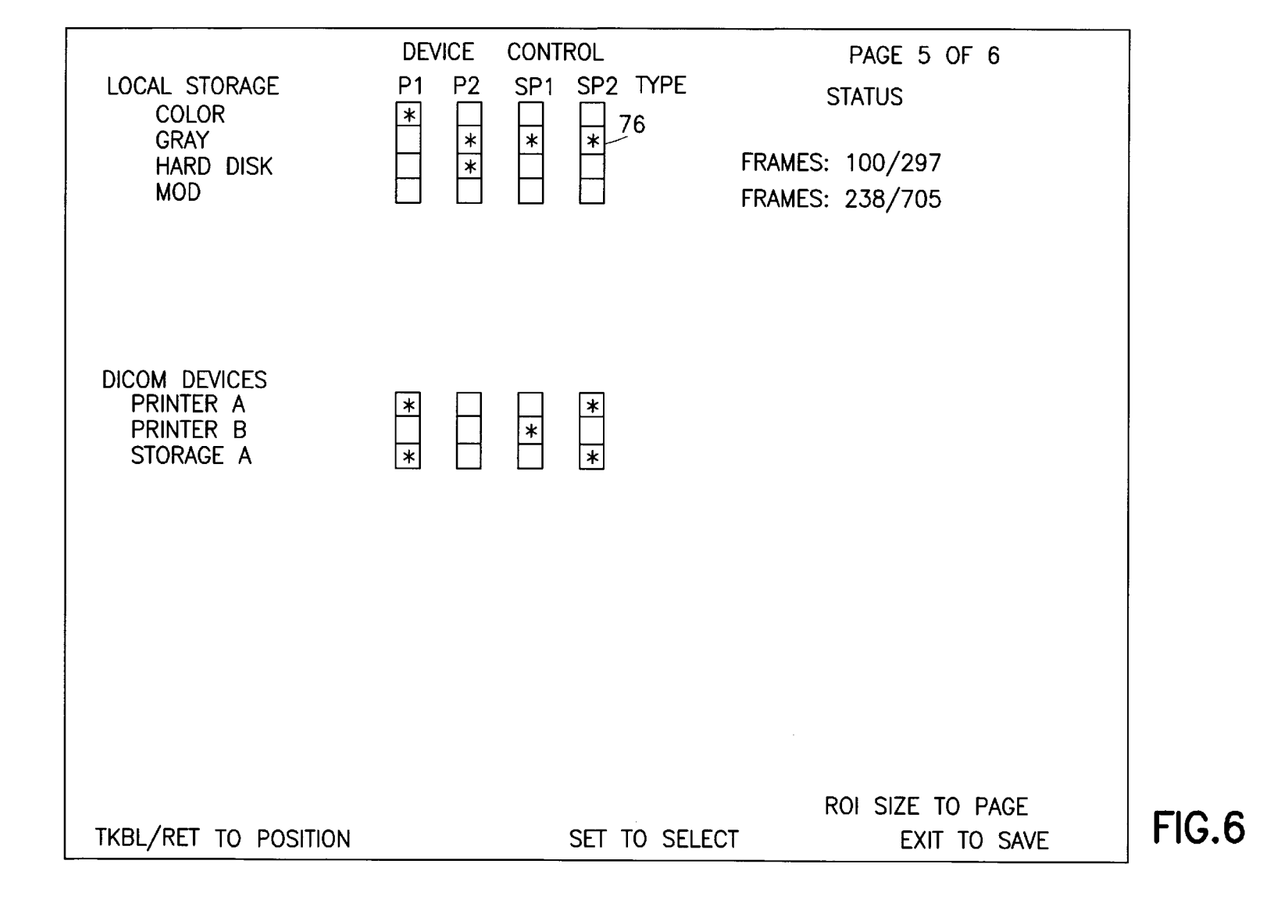
FIG. 6 is a schematic reproducing a "Device Control" menu which can be used to configure the Print/Store buttons on the operator interface in accordance with the preferred embodiment of the invention.

Referring again to FIG. 3, the preferred embodiment is equipped with a plurality of Print/Store buttons on the operator interface 22. Each Print/Store button can be configured by the device control mapping manager 37 to initiate image transfer to more than one remote device, e.g., when a particular Print/Store button is pressed, the computer will send the corresponding acquired image to all activated remote devices configured for that button. The device control mapping manager is programmed to retrieve a Device Control menu, which is a virtual representation of the various configurations for the Print/Store buttons, from the hard disk 36 and send it to the display monitor 18. An exemplary Device Control menu for an imager having the functional equivalent of four Print/Store buttons, P1, P2, SP1 and SP2, is shown in FIG. 6. The P1 and P2 control states are respectively activated by pressing buttons P1 and P2 on the operator interface; the SP1 and SP2 control states are respectively activated by pressing buttons P1 and P2 while the Shift key is also depressed. Each of these four control states in turn can be configured so that the data of the acquired image is expressed as either color intensity values or gray-scale intensity values; so that the acquired image will be stored on the hard disk or the MOD; so that the acquired image will be transferred to one or more activated remote devices (e.g., Printers A and B and Storage A denoted in FIG. 6); or any combination of these options. For example, the imager represented in FIG. 6 is configured as follows: a color image will be transferred to Printer A and Storage A subsequent to depression of button P1; a gray-scale image will be transferred to Printer A and Storage A subsequent to depression of button P2 and the Shift key; a gray-scale image will be stored on the hard disk subsequent to depression of button P2; and a gray-scale image will be transferred to Printer B subsequent to depression of button P1 and the Shift key. Each Print/Store button configuration can be set via the operator interface. Any one of the device control fields 76 can be set by highlighting that field using the trackball and then pressing the Set key. The particular configuration of each Print/Store button is indicated by a symbol displayed in each set device control field. For each remote device ("DICOM Device" on the Device Control menu) configured to a particular Print/Store button, pressing that button after freezing an image will cause the associated DICOM task to retrieve an image file having a copy of that image from the hard disk and convert that image file to a DICOM object compatible with the associated remote device.

In accordance with the preferred embodiment, the device control mapping manager constructs a mapping of DICOM tasks (configured for respective remote devices) to Print/Store buttons. In other words, when the operator interacts with the Device Control menu (shown in FIG. 6) to configure a Print/Store button to a particular remote device, the device control mapping manager then identifies the DICOM task corresponding to that remote device and includes it in the device control mapping. The device control mapping manager 37 provides the device control mapping to the archive manager 34. When the archive manager later receives a posting from the control platform 32 that a particular Print/Store button has been pressed, the archive manager 34 will then refer to the device control mapping and determine the DICOM tasks associated with that button from the mapping. The archive manager 34 then advises the DICOM queue manager 38 which DICOM tasks 40 need to construct objects incorporating the selected image frame. The DICOM queue manager 38 then copies that image file once for each task and, if the remote devices are storage devices or single-image printers, adds a job element to the Active Queue of each task. For multi-image printers, the DICOM queue manager 38 need only add another image file name to the Image File Name field of an existing job element in the queue.

Although FIG. 3 depicts only one DICOM task, in accordance with the preferred embodiment, the imager is programmed with multiple DICOM tasks. In the preferred embodiment, one DICOM task is dedicated to worklist management and ten DICOM tasks can be configured to convert image files into either DICOM print objects or DICOM storage objects. It should be appreciated, however, that the present invention is not restricted to having ten DICOM tasks for printing and storage. In response to pressing of a Print/Store button which is configured for multiple remote devices, a corresponding multiplicity of DICOM tasks will be started substantially simultaneously. These concurrently running tasks are performed using conventional multi-tasking principles.

In accordance with the preferred embodiment, the host computer of the imager is programmed to store in memory the configuration data input via the Device Configuration menu shown in FIG. 5. For each configured remote device which is activated, a respective DICOM task is configured by the DICOM presets manager 39 in accordance with the stored configuration data. In other words, each DICOM task is partly defined by the inputs to the corresponding page of the Device Configuration menu. In particular, each DICOM task is programmed to convert an image file into a print object for printers, if "Printer" was entered in the Device Type field (see FIG. 5) on the Device Configuration menu, and into a storage object for storage devices, if "Storage" was entered in the Device Type field. In the case where more than one remote device is designated to receive the same image, the associated DICOM tasks will convert respective copies of that image into respective DICOM objects acceptable to the respective remote devices.

The image transfer procedure used in the preferred embodiment will be described in more detail with reference to FIG. 3. In response to a request from the operator to archive a frozen image, the control platform 32 sends an "Image Store" instruction to the archive manager 34. In response to the "Image Store" instruction, the archive manager retrieves the frozen image from cine memory 16 and stores it either on the hard disk 36 or on the MOD 46, depending on the system operator's selection.

In addition, the system operator may request that the frozen image be sent to an activated remote device for printing or storage by pressing the appropriate Print/Store button. In response to a first request from the operator to transfer a frozen image to a remote device which has been configured for "Live Imaging", the control platform 32 sends an "Image Send" instruction to the archive manager 38. The archive manager 34 retrieves the frozen image from the cine memory 16 and stores it in a file on the hard disk 36. The file includes the image pixel data as well as certain attribute data, such as patient name, patient ID, gray-scale or color image, number of rows and columns of pixels, etc. Then the archive manager 34 notifies the DICOM queue manager 38 of the image and which remote device that image is configured to go to. Next the queue manager 38 copies the image to another location on the hard disk and gives that copied image a new file name. If the pressed Print/Store button is configured for multiple remote devices, then the queue manager 38 will store multiple copies of the frozen image in multiple files, i.e., a separate copy of the frozen image for each remote device designated as a destination for that image.

In accordance with the DICOM standard, each DICOM task is designed to convert an image file, comprising image frame data and attribute data, into a DICOM-formatted object, also comprising image frame and attribute data. That DICOM object must conform not only to the DICOM standards, but also to the attribute requirements of the remote device destined to receive that DICOM object.

Jobs which are waiting to be converted into DICOM objects by a DICOM task are queued in a so-called Active Queue. The queue is managed by a DICOM queue manager 38. For each job, the queue manager 38 adds a separate entry in the Active Queue. In particular, each entry comprises an element having multiple fields. One of those fields lists the image file names for the images in the particular job. Each image file name serves as a pointer for retrieval from memory of the named image. Another field in the element identifies the remote device (by identifying the Task ID of the DICOM task associated with that remote device) which that stored image is destined to be sent to.

The first entry in the Active Queue is sent by the queue manager 38 to a DICOM task 40. The DICOM task 40 is preferably software for performing the task of formatting the image identified in that first entry so that the image will be in proper DICOM format and will be acceptable to the destination remote device, also identified in the first entry.

When the DICOM task 40 receives an entry from the Active Queue, it will read the Image File Name field (i.e., the pointer), which will contain the file name of the image to be formatted and transferred to the destination remote device. The DICOM task 40 then retrieves the image from the named file on the hard disk and reformats it into the appropriate DICOM object (according to the type of remote device). For example, in addition to the pixel data for the image to be transferred, the DICOM image manager will convert attribute data into DICOM format. If the remote device is a storage device, the DICOM image manager will also attach a UID to the image.

Next the DICOM task will open a connection (association) to the destination remote device and negotiate a syntax. In particular, the DICOM task 40 sends a request via the network manager 42 and a port 44 that an association with the configured remote device be opened. If the remote device responds affirmatively and if a communications syntax is agreed upon, the association is opened.

Once the association is open and assuming that a channel on the network is available (i.e., the network is not busy), the image is sent from the imager onto the network via the network manager 40 and the port 42. If the destination remote device sends back a message that the image transfer was successful, then the DICOM task 40 notifies the queue manager 38. The queue manager then removes the entry for the successfully transferred image from the Active Queue and deletes that image from the hard disk 36. If the message from the destination remote device indicates that the image transfer was unsuccessful, then the queue manager 38 moves the entry for the successfully transferred image from the Active Queue to a Holding Queue and does not delete that image from the hard disk 36.

In the "Live Imaging" mode, the association between the imager and the destination remote device is kept open until the "End Exam" button on the operator interface 22 is pressed. While "Live Imaging" is active and for a remote device which accept images singly (i.e., one at a time), the foregoing "Image Send" procedure will be repeated each time the operator inputs a request to transfer a frozen image to the configured remote device.

Figure 4:
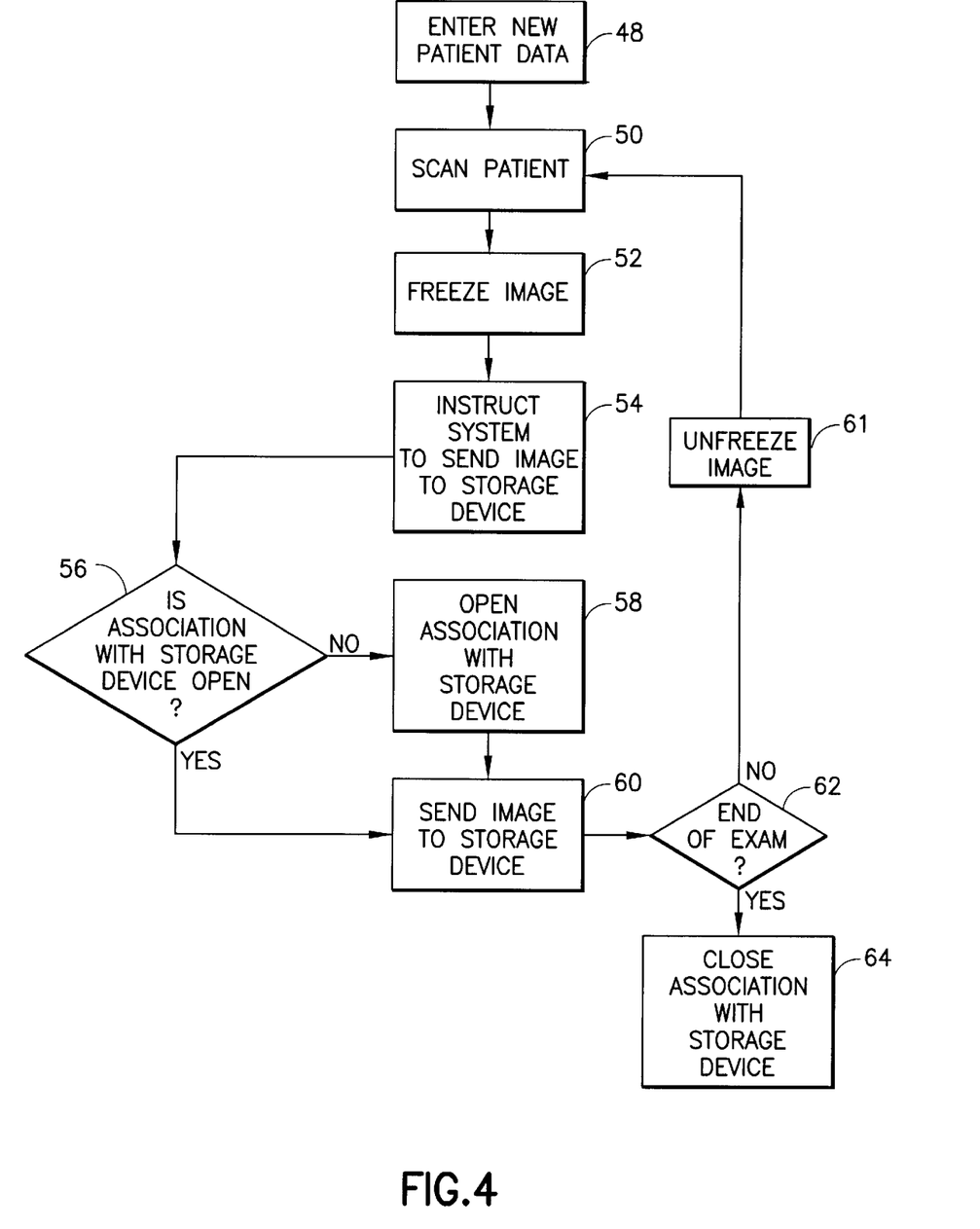
FIG. 4 is a flowchart showing the steps involved in the method according to the preferred embodiment of the invention.

The "End Exam" is a button that is pushed by the user to indicate that the examination for the current patient has ended. The process for performing an examination and sending a selected image to a storage device is shown in FIG. 4. At the beginning of every exam the user (sonographer or sonologist) will push the "New Patient" button. When this button is pushed, a menu will appear on the screen of the display monitor (18 in FIG. 1). At this time, the user enters (step 48) information about the patient (e.g., name, patient identifier, accession number, birthdate, etc.). When data entry is completed, the user exits the menu. At this time, a DICOM Study Instance UID is created. This Study Instance UID forms the base of the SOP Instance UID which tells the receiving DICOM device (SCP) that the image received belongs to a particular patient. Every image taken by the user, after exiting the "New Patient" menu, will have the same UID.

The examination may then begin. The user will scan the patient (step 50), as needed. The user, at any time, can freeze the image (step 52) and take a snapshot of that image to send to a storage device (step 54). The SOP Instance UID will direct the image to the proper patient's folder of images. Storage devices receive images one at a time. The typical method of image transfer to a storage device is as follows: the queue manager opens an association (connection) with the receiving storage device; transfer negotiations occur; the image is transferred; and the association is closed. In contrast, the imager in accordance with the preferred embodiment of the present invention can be configured to open the association once and keep it open throughout the entire exam. In this case, the association is opened upon the sending of the first image. Now, all images selected to be sent after the association has been opened, and before the "End Exam" button is pushed, will be transferred during that one association. No other associations need to be made, thereby increasing transfer efficiency.

Referring again to FIG. 4, in response to each depression of the Print/Store button configured to the destination storage device, the DICOM task 40 will determine if the association with that storage device is open (step 56). If not, the DICOM task 40 will open the association (step 58), as previously described. If the association is open, then the DICOM task 40 will attempt to send the DICOM object to the storage device. If the network is busy and the DICOM object cannot be sent, the DICOM object will remain queued and succeeding images will also be queued during this time. If the network will allow the DICOM object to be sent to the destination storage device, then the DICOM object constructed by the DICOM task 40 from the image identified by the first entry on the Active Queue will be transmitted to the storage device via the DICOM network (step 60). The queue manager 38 then determines whether the "End Exam" button has been pressed (step 62). If it has, the queue manager instructs all DICOM tasks to close any associations (step 64). If the "End Exam" button has not been depressed, the association will not be closed and the system operator can again scan the patient after unfreezing the image (step 61).

The "Live Imaging" procedure differs from that described above when the receiving remote device is a printer which prints multi-image film sessions (e.g., 3×5=15 images). If this were the case, the user would normally have to take all 15 images before the imager would send the job to the printer. In the "Live Imaging" mode, the association with the remote printer will not be opened until all images of the multi-image film session have been acquired. Thereafter the association with the remote printer will be held open until the "End Exam" button is pressed. If, at the time when the "End Exam" button is pressed, an incomplete film session has been acquired (i.e., the number of image file names listed in an element in the Partial Print Queue, corresponding to a particular destination printer which prints film having N images, is less than N), then this incomplete film session will be queued for subsequent transfer on the DICOM network. When a channel on the network is available, the DICOM task for that printer will transmit the multiple images making up the incomplete film session. Consequently, in accordance with the preferred embodiment of the invention, to transfer an incomplete film session to a remote printer, the system operator need press only one button, to wit, the "End Exam" button.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for sending image frame data from an imaging system to remote devices, comprising the steps of:

interacting with a graphical user interface to configure said imaging system to transfer successive acquired images to a first remote device in a first format compatible with said first remote device while maintaining an open association with said first remote device throughout a series of image acquisitions;

acquiring a first frame of image data;

in response to a first manipulation of a first operator input device, constructing a first data object incorporating said first frame of image data in said first format, opening an association with said first remote device, and sending said first data object to said first remote device via a network while said association with said first remote device is open;

acquiring a second frame of image data; and in response to a second manipulation of said first operator input device, constructing a second data object incorporating said second frame of image data in said first format, and sending said second data object to said first remote device via said network while said association with said first remote device is still open.

2. The method as recited in claim 1, further comprising the steps of:

interacting with said graphical user interface to configure said imaging system to transfer successive groups of acquired images to a second remote device in a second format compatible with said second remote device while maintaining an open association with said second remote device throughout a series of image acquisitions;

acquiring a group of first through N-th frames of image data;

after each frame acquisition of said group, manipulating a second operator input device;

in response to the first (N−1) manipulations of said second operator input device, constructing a group of first through (N−1)-th data objects incorporating said group of first through (N−1)-th frames in said second format and queuing said group of first through (N−1)-th data objects; and in response to the N-th manipulation of said second operator input device, constructing an N-th data object incorporating the N-th frame of said group in said second format, opening an association with said second remote device, and sending said group of first through N-th data objects to said second remote device via said network while said association is open.

3. The method as recited in claim 2, further comprising the steps of:

acquiring at least an (N+1)-th frame of image data;

after said (N+1)-th frame acquisition, manipulating said second operator input device;

in response to the (N+1)-th manipulation of said second operator input device, constructing an (N+1)-th data object incorporating the (N+1)-th frame in said second format and queuing said (N+1)-th data object; and in response to manipulation of a third operator input device, sending said (N+1)-th data object to said second remote device via said network while said association is open and then closing said associations with first and second remote devices.

4. The method as recited in claim 1, further comprising the steps of:

interacting with said graphical user interface to configure said imaging system to transfer successive acquired images to a second remote device in a second format compatible with said second remote device while maintaining an open association with said second remote device throughout a series of image acquisitions;

acquiring a third frame of image data;

in response to a first manipulation of a second operator input device, constructing a third data object incorporating said third frame of image data in said second format, opening an association with said second remote device, and sending said third data object to said second remote device via a network while said association with said second remote device is open;

acquiring a fourth frame of image data; and in response to a second manipulation of said second operator input device, constructing a fourth data object incorporating said fourth frame of image data in said second format, and sending said fourth data object to said second remote device via said network while said association with said second remote device is still open.

5. The method as recited in claim 4, further comprising the step of, in response to manipulation of a third operator input device, closing said associations with said first and second remote devices.

6. The method as recited in claim 4, wherein said steps of constructing first and third data objects are performed by first and second object-constructing tasks respectively, further comprising the step of constructing a device control mapping which maps said first and second object-constructing tasks to said first and second operator input devices respectively.

7. The method as recited in claim 1, wherein said interacting step comprises the step of clicking a virtual toggle switch on said graphical user interface to change from a first state to a second state, said first state enabling a first imaging mode wherein an association with said first remote device is not maintained open during successive image acquisitions, and said second state enabling a second imaging mode wherein an association with said first remote device is maintained open during successive image acquisitions.

8. A method for sending image frame data from an imaging system to a remote printer, comprising the steps of:

interacting with a graphical user interface to configure said imaging system to transfer successive groups of acquired images to said remote printer in a format compatible with said remote printer while maintaining an open association with said remote printer throughout a series of image acquisitions;

acquiring first through N-th frames of image data;

after each frame acquisition, manipulating a first operator input device;

in response to the first (N−1) manipulations of said first operator input device, constructing first through (N−1)-th data objects incorporating the first through (N−1)-th frames in said format and queuing said first through (N−1)-th data objects; and in response to the N-th manipulation of said first operator input device, constructing an N-th data object incorporating the N-th frame in said format, opening an association with said remote printer, and sending said first through N-th data objects to said remote printer via said network while said association is open.

9. The method as recited in claim 8, further comprising the steps of:

acquiring at least an (N+1)-th frame of image data;

after said (N+1)-th frame acquisition, manipulating said first operator input device;

in response to the (N+1)-th manipulation of said first operator input device, constructing an (N+1)-th data object incorporating the (N+1)-th frame in said format and queuing said (N+1)-th data object; and in response to manipulation of a second operator input device, sending said (N+1)-th data object to said remote printer via said network while said association is open and then closing said association with said remote printer.

10. An imaging system capable of sending image frame data to a remote device via a network, comprising:

a networking port for communicating with a network;

a graphical user interface for configuring said imaging system to transfer successive acquired images to a remote device on said network in a format compatible with said remote device while maintaining an open association with said remote device via said network throughout a series of image acquisitions;

an operator interface comprising first and second operator input devices;

means for acquiring first and second frames of image data;

an object constructing task for constructing first and second data objects respectively incorporating said first and second frames of image data in said format; and means for transferring said first and second data objects to said networking port for transmission to said remote device, wherein in response to a first manipulation of said first operator input device, said object constructing task constructs said first data object, opens an association with said remote device via said network, and sends said first data object to said remote device via a network while said association with said remote device is open, and in response to a second manipulation of said first operator input device, said object constructing task constructs said second data object and sends said second data object to said remote device via said network while said association with said remote device is still open.

11. The system as recited in claim 10, wherein said association with said remote device is closed in response to manipulation of said second input device.

12. An imaging system capable of sending image frame data to remote devices via a network, comprising:

a networking port for communicating with a network;

a graphical user interface comprising a first menu for configuring said imaging system to transfer successive acquired images to a first remote device on said network in a first format compatible with said first remote device while maintaining an open association with said first remote device via said network throughout a series of image acquisitions, and a second menu for configuring said imaging system to transfer successive acquired images to a second remote device on said network in a second format compatible with said second remote device while maintaining an open association with said second remote device via said network throughout a series of image acquisitions;

an operator interface comprising first, second and third operator input devices;

means for acquiring first through fourth frames of image data;

a first object constructing task for constructing first and second data objects respectively incorporating said first and second frames of image data in said first format;

a second object constructing task for constructing third and fourth data objects respectively incorporating said third and fourth frames of image data in said second format; and means for transferring said first through fourth data objects to said networking port, wherein in response to a first manipulation of said first operator input device, said first object constructing task constructs said first data object, opens an association with said first remote device via said network, and sends said first data object to said first remote device via a network while said association with said first remote device is open, and in response to a second manipulation of said first operator input device, said first object constructing task constructs said second data object and sends said second data object to said first remote device via said network while said association with said first remote device is still open, and in response to a first manipulation of said second operator input device, said second object constructing task constructs said third data object, opens an association with said second remote device via said network, and sends said third data object to said second remote device via a network while said association with said second remote device is open, and in response to a second manipulation of said second operator input device, said second object constructing task constructs said fourth data object and sends said fourth data object to said second remote device via said network while said association with said second remote device is still open.

13. The system as recited in claim 12, wherein said associations with said first and second remote devices are closed in response to manipulation of said third input device.

14. An imaging system capable of sending image frame data to a remote printer via a network, comprising:

a networking port for communicating with a network;

a graphical user interface for configuring said imaging system to transfer acquired images to a remote printer on said network in a format compatible with said remote printer while maintaining an open association with said remote printer via said network;

an operator interface comprising first and second operator input devices;

means for acquiring first through N-th frames of image data;

an object constructing task for constructing first through N-th data objects respectively incorporating said first through N-th frames of image data in said format; and means for transferring said first through N-th data objects to said networking port for transmission to said remote printer, wherein in response to first through (N−1)-th manipulations of said first operator input device, said object constructing task constructs first through (N−1)-th data objects incorporating the first through (N−1)-th frames in said format and queues said first through (N−1)-th data objects, and in response to the N-th manipulation of said first operator input device, said object constructing task constructs an N-th data object incorporating the N-th frame in said format, opens an association with said remote printer via said network, and sends said first through N-th data objects to said remote printer via said network while said association is open.

15. The system as recited in claim 14, further comprising means for acquiring at least an (N+1)-th frame of image data, wherein in response to an (N+1)-th manipulation of said first operator input device, said object constructing task constructs an (N+1)-th data object incorporating the (N+1)-th frame in said format and queuing said (N+1)-th data object, and in response to manipulation of said second operator input device, sends said (N+1)-th data object to said remote printer via said network while said association is open and then closes said association with said remote printer.

* * * * *